US009834739B2

(12) United States Patent
Aida et al.

(10) Patent No.: US 9,834,739 B2
(45) Date of Patent: Dec. 5, 2017

(54) FRAGRANCE COMPOSITION

(71) Applicant: Takasago International Corporation, Ota-ku, Tokyo (JP)

(72) Inventors: Takashi Aida, Kanagawa (JP); Kenji Maruyama, Kanagawa (JP); Hiroyuki Matsuda, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 15/111,217

(22) PCT Filed: Jan. 15, 2015

(86) PCT No.: PCT/JP2015/050859
§ 371 (c)(1),
(2) Date: Jul. 13, 2016

(87) PCT Pub. No.: WO2015/108092
PCT Pub. Date: Jul. 23, 2015

(65) Prior Publication Data
US 2016/0333291 A1  Nov. 17, 2016

(30) Foreign Application Priority Data

Jan. 16, 2014  (JP) ................................. 2014-006143

(51) Int. Cl.
| | | |
|---|---|---|
| *C11D 3/50* | (2006.01) | |
| *C11B 9/00* | (2006.01) | |
| *A61Q 13/00* | (2006.01) | |
| *A61K 8/34* | (2006.01) | |
| *A23L 27/20* | (2016.01) | |
| *A61Q 5/02* | (2006.01) | |
| *A61Q 19/10* | (2006.01) | |

(52) U.S. Cl.
CPC .......... *C11B 9/0061* (2013.01); *A23L 27/204* (2016.08); *A61K 8/347* (2013.01); *A61Q 5/02* (2013.01); *A61Q 13/00* (2013.01); *A61Q 19/10* (2013.01); *C11D 3/50* (2013.01)

(58) Field of Classification Search
CPC ......... A23L 27/204; A61K 8/34; A61K 8/347; C11D 3/50; C11B 9/0061
See application file for complete search history.

(56) References Cited

U.S. PATENT DOCUMENTS

| | | | |
|---|---|---|---|
| 4,473,588 A | 9/1984 | Wilson et al. | |
| 4,650,604 A | 3/1987 | Broekhof et al. | |
| 4,657,700 A | 4/1987 | Ochsner | |
| 6,844,019 B1 | 1/2005 | Cheetham et al. | |
| 2009/0004360 A1 | 1/2009 | Bingley et al. | |
| 2010/0113616 A1 | 5/2010 | Gerke et al. | |
| 2013/0011352 A1 | 1/2013 | Gaudin | |

FOREIGN PATENT DOCUMENTS

| | | |
|---|---|---|
| JP | 60-097932 A | 5/1985 |
| JP | 61-103819 A | 5/1986 |
| JP | 04-503900 A | 7/1992 |
| JP | 09-111285 A | 4/1997 |
| JP | 10-273878 A | 10/1998 |
| JP | 2001-089970 A | 4/2001 |
| JP | 2001-279576 A | 10/2001 |
| JP | 2002-537770 A | 11/2002 |
| JP | 2010-526199 A | 7/2010 |
| JP | 2010-527242 A | 8/2010 |
| JP | 2011-256392 A | 12/2011 |
| JP | 2013-525535 A | 6/2013 |
| JP | 2014-169393 A | 9/2014 |
| WO | WO 89/00820 A1 | 2/1989 |

OTHER PUBLICATIONS

R.Thompson et al., Journal of Chromatography (1988) 369-382.*
T. Sostaric et al., Journal of Agricultural Food Chemistry (2000) vol. 48, 5802-5807.*
Written Opinion, PCT/JP2015/050859, dated Apr. 2015.*
Arctander, Steffen, "Perfume and Flavor Chemicals (Aroma Chemicals) II," 1994, 3073.
Indo, Motoichi, "Synthetic Aromachemical: Chemicals and Product Knowledge, Expanded and Revised Edition," 2005, 146-147, with partial English translation.
Okuda, Osamu, "Comprehensive List of Flavor and/or Fragrance Chemicals II," 1968, 680, with partial English translation.
Tamura et al., "Aroma Profile of Vanilla in Bourbon Beans," Recent Advances in Food and Flavor Chemistry, Apr. 21, 2010, 326:139-149.

* cited by examiner

*Primary Examiner* — John R Hardee
(74) *Attorney, Agent, or Firm* — Foley & Lardner LLP

(57) ABSTRACT

The present invention relates to a fragrance composition that has a vanilla odor property, that is chemically stable and that can be blended in a variety of products, which can be an alternative material for vanillin or ethyl vanillin. The fragrance composition of the present invention comprises: A) one or more selected from the group consisting of vanillyl alcohol, ethylvanillyl alcohol, isovanillyl alcohol and veratryl alcohol; and B) one or more selected from the group consisting of 2-ethoxy-4-methylphenol, 2-methoxy-4-methylphenol, 2-ethoxy-5-methylphenol, 2-ethoxy-4-ethylphenol, 2-ethoxy-5-ethylphenol, 2-methoxy-p-cresol methyl carbonate and 2-ethoxy-5-(1-propenyl)-phenol, wherein the total content of component A and component B in the fragrance composition is 0.01-90% by mass, and the mixing ratio of component A and component B (on a mass basis) is in a range of 99:1-70:30.

9 Claims, No Drawings

FRAGRANCE COMPOSITION

CROSS-REFERENCE TO RELATED APPLICATIONS

This application is a National Stage application of PCT/JP2015/050859, filed Jan. 15, 2015, which claims priority from Japanese application JP 2014-006143, filed Jan. 16, 2014.

TECHNICAL FIELD

The present invention relates to a fragrance composition. More particularly, the present invention relates to a fragrance composition that can impart a vanilla-like odor property and that can suppress deterioration and discoloration of the fragrance, and to fragrances and cosmetics, a toiletry product and the like blended with said fragrance composition.

BACKGROUND ART

An odor property of vanilla is very valuable in the flavor and/or fragrance industry. In order to impart this odor property to a flavor and/or fragrance composition or product, vanillin, ethyl vanillin or a combination of two of them is generally used, which has favorably been applied, for example, to fragrancing of fragrance products such as perfume, cologne and air freshener.

Recently, due to the growing needs of consumers, there are needs for fragrancing a huge variety of products such as laundry detergents, household detergents, shampoo, body soap, soap, toothpaste and hair styling agents with an odor property of vanilla.

Vanillin and ethyl vanillin, however, are known to induce deterioration of odor and unfavorable coloring, and susceptive to decomposition, alteration, discoloration or polymerization or the like under an alkaline condition, an oxygen-existing condition, a temperature condition or a light exposure condition or the like, as a result of which the vanilla-like odor used for odoring changes. This has been a problem where vanillin and ethyl vanillin cannot be used depending on the vehicle. Specifically, vanillin and ethyl vanillin are unstable in vehicles of soap, shampoo and alcoholic compositions. So when a fragrance composition containing vanillin, ethyl vanillin or a combination of two of them is used in such a vehicle, deterioration and brown discoloration of the odor will be caused within short time, and the vanilla odor property will vanish.

Under such circumstances, there has been a need for a development of a fragrance composition that has a vanilla odor property, and that is chemically stable even when blended in a product containing a vehicle of soap, shampoo or an alcoholic composition.

Until now, a number of techniques for preventing alteration and discoloration of vanillin have been proposed.

For example, a method in which an iodized salt is added to a chemical drug containing vanillin in order to prevent discoloration of vanillin (Patent Literature 1: Japanese Unexamined Patent Application (Translation of PCT) Publication No. 2010-526199) and a method in which an antioxidant such as butylated hydroxytoluene (BHT) is added in order to suppress deterioration of an aldehyde perfume chemical component containing vanillin (Patent Literature 2: Japanese Unexamined Patent Application Publication No. 2011-256392) have been proposed.

In addition, discoloration of a textile product due to contact with wood or cardboard during storage of the textile product is also considered to be caused by vanillin generated upon decomposition of lignin contained in wood or cardboard. As a technique for preventing this, methods have been proposed in which a textile is treated with a phosphate ester ammonium salt-type anion surfactant, a sulfate ester ammonium-type anion surfactant, a sulfonate ammonium-type anion surfactant or a fluorine-containing water-and-oil repellent to absorb vanillin that causes coloring (Patent Literature 3: Japanese Unexamined Patent Application Publication No. 2001-279576, Patent Literature 4: Japanese Unexamined Patent Application Publication No. 2001-89970 and Patent Literature 5: Japanese Unexamined Patent Application Publication No. Heisei 10-273878).

These methods, however, lack sustainability against alteration caused by vanillin. Moreover, there are cases where blending an additive is unacceptable depending on a product base. Furthermore, there is a problem that the textile fabricating techniques cannot be applied to flavors and/or fragrances.

In response to this, instead of using an additive, it has been proposed to derivatize vanillin itself to obtain a vanillin-like flavor and/or fragrance that is less likely to alter or discolor.

For example, compounds such as 4-formyl-2-methoxyphenyl 2-methylpropanoate ("ISOBUTAVAN": manufactured by Givaudan) (see Patent Literature 6: specification of U.S. Pat. No. 4,473,588), 2-ethoxy-4-methylphenol ("Ultravanil": manufactured by Givaudan) (see Patent Literature 7: Japanese Unexamined Patent Application Publication No. Showa 61-103819) and 2-ethoxy-4-(methoxymethyl)phenol ("METHYLDIANTILIS": manufactured by Givaudan) (see Patent Literature 8: specification of U.S. Pat. No. 4,657,700) are used as alternatives to unstable vanillin or ethyl vanillin, primarily in combination with vanillin or ethyl vanillin.

However, each of them has characteristic shortcomings. For example, 4-formyl-2-methoxyphenyl 2-methylpropanoate is a compound in which the phenol group of vanillin has been esterified, which is susceptible to hydrolysis in a vehicle. Hydrolysis of this compound will free vanillin and generate isobutyric acid, which will result strong unpleasant fatty acid malodor. Although an o-alkoxy phenol such as 2-ethoxy-4-methylphenol is chemically stable, it has unpleasant phenol malodor in addition to a vanillin-like odor property. 2-Ethoxy-4-(methoxymethyl)phenol also lacks chemical stability and is very susceptible to coloring, and the odor property is not comparable to the odor quality and the strength of vanillin or ethyl vanillin. Therefore, it is difficult to use these compounds independently as an alternative compound for vanillin.

Japanese Unexamined Patent Application (Translation of PCT) Publication No. 2013-525535 (Patent Literature 9) describes alkyl aryl carbonates, such as 2-methoxy-p-cresol methyl carbonate, as compounds having a vanillin-like odor property. Although this compound is chemically stable, the vanillin-like odor strength is weak so it is difficult to be used independently as an alternative compound for vanillin.

Moreover, Motoichi INDO, "Synthetic Aromachemical: Chemicals and Product Knowledge, Expanded and Revised edition", The Chemical Daily Co. Ltd., pages 146-147, expanded and revised edition published on Mar. 22, 2005 (Non-Patent Literature 2) describes 2-ethoxy-5-(1-propenyl) phenol (also known as "vanitrope"). Although this compound is chemically stable, its odor quality is less sweet compared to vanillin and has unpleasant phenol malodor, and thus is difficult to be used independently as an alternative compound for vanillin.

Meanwhile, Osamu OKUDA, "Comprehensive List of Flavor and/or Fragrance Chemicals [II]", Hirokawa-Shoten Ltd., published on Jan. 15, 1968, page 680 (Non-Patent Literature 1) lists a variety of vanillyl alcohol derivatives such as vanillyl alcohol, ethylvanillyl alcohol, isovanillyl alcohol and veratryl alcohol. The document describes that these compounds can be used as a retaining agent or a raw material for synthesis of a flavor and/or fragrance but it does not describe the use of these compounds as odor components. In addition, it does not describe as to what kind of specific odor property these compounds have.

Steffen Arctander, "Perfume and Flavor Chemicals (Aroma Chemicals) II", Allured Publishing Corporation, published in 1994, page 3073 (Non-Patent Literature 3) describes that vanillyl alcohol has a vanilla-like odor property. However, it describes that the odor strength of vanillyl alcohol is much lower compared to that of vanillin.

CITATION LIST

Patent Literature

[Patent Literature 1] Japanese Unexamined Patent Application (Translation of PCT) Publication No. 2010-526199
[Patent Literature 2] Japanese Unexamined Patent Application Publication No. 2011-256392
[Patent Literature 3] Japanese Unexamined Patent Application Publication No. 2001-279576
[Patent Literature 4] Japanese Unexamined Patent Application Publication No. 2001-89970
[Patent Literature 5] Japanese Unexamined Patent Application Publication No. Heisei 10-273878
[Patent Literature 6] Specification of U.S. Pat. No. 4,473,588
[Patent Literature 7] Japanese Unexamined Patent Application Publication No. Showa 61-103819
[Patent Literature 8] Specification of U.S. Pat. No. 4,657,700
[Patent Literature 9] Japanese Unexamined Patent Application (Translation of PCT) Publication No. 2013-525535

Non-Patent Literature

[Non-Patent Literature 1] Osamu OKUDA, "Comprehensive List of Flavor and/or Fragrance Chemicals [II]", Hirokawa-Shoten Ltd., published on Jan. 15, 1968, page 680
[Non-Patent Literature 2] Motoichi INDO "Synthetic Aromachemical: Chemicals and Product Knowledge, Expanded and Revised Edition", The Chemical Daily Co. Ltd., expanded and revised edition published on Mar. 22, 2005, pages 146-147
[Non-Patent Literature 3] Steffen Arctander, "Perfume and Flavor Chemicals (Aroma Chemicals) II", Allured Publishing Corporation, published in 1994, page 3073

SUMMARY OF INVENTION

Technical Problem

As described above, discovery of a material as an alternative to vanillin or ethyl vanillin has been a long-time problem in the flavor and/or fragrance industry. Specifically, development of a fragrance composition that has a vanilla odor property, that is chemically stable, and that can be blended in a variety of products has been strongly desired.

Solution to Problem

Under such circumstance, the present inventors have gone through keen studies to solve the above-described problem, as a result of which found: 1) that a vanillyl alcohol has a vanillin-like odor property, is chemically stable, and is not susceptible to alteration or discoloration; 2) that addition of a 2-alkoxy phenol or a methyl carbonate ester thereof to a vanillyl alcohol at a specific ratio can result a chemically stable isoeugenol-like vanillin-like odor property with sufficient odor strength; and 3) that mixing a vanillyl alcohol with a 2-alkoxy phenol or a methyl carbonate ester thereof can mask the unpleasant phenol malodor inherent to some of the 2-alkoxy phenols and the methyl carbonate esters thereof, thereby accomplishing the present invention.

Specifically, the present invention relates to a fragrance composition stated below and a product such as fragrances and cosmetics, a toiletry product, a quasi-drug or goods blended with said fragrance composition.

[1] A fragrance composition, comprising:
A) one or more selected from the group consisting of vanillyl alcohol, ethylvanillyl alcohol, isovanillyl alcohol and veratryl alcohol; and
B) one or more selected from the group consisting of 2-ethoxy-4-methylphenol, 2-methoxy-4-methylphenol, 2-ethoxy-5-methylphenol, 2-ethoxy-4-ethylphenol, 2-ethoxy-5-ethylphenol, 2-methoxy-p-cresol methyl carbonate and 2-ethoxy-5-(1-propenyl)-phenol (also known as vanitrope),
wherein the total content of component A and component B in the fragrance composition is 0.01-90% by mass, and the mixing ratio of component A and component B (on a mass basis) is in a range of 99:1-70:30.
[2] The fragrance composition according to [1], wherein component A is ethylvanillyl alcohol and component B is 2-ethoxy-4-methylphenol.
[3] The fragrance composition according to either one of [1] and [2], which has vanilla-like odor.
[4] The fragrance composition according to any one of [1] to [3], further comprising C) one or more selected from the group consisting of vanillin, ethyl vanillin, isovanillin and methyl vanillin.
[5] A product that is any of fragrances and cosmetics, a toiletry product, a quasi-drug or goods blended with the fragrance composition according to any one of [1] to [4].
[6] The fragrance composition according to any one of [1] to [4], which is highly stable against light and heat.

Advantageous Effect of Invention

A fragrance composition of the present invention obtained by mixing a vanillyl alcohol with a 2-alkoxy phenols or a methyl carbonate ester thereof at a specific ratio has a vanilla-like odor property with significantly excellent performance. Furthermore, since the fragrance composition of the present invention is chemically stable, it can be blended in a variety of products. In addition, there is no problem in using the fragrance composition of the present invention with conventional vanillins.

Since the fragrance composition of the present invention can be effective even with a small amount, it enables adding odor to a product that needs odoring with a perfume chemical such as fragrances and cosmetics, a toiletry product, a quasi-drug or goods.

In a preferable aspect of the present invention, a fragrance composition of the present invention can be used to impart expansion and cohesiveness to a formulated flavor and/or fragrance that contains the fragrance composition owing to the odor quality unique to vanilla with an excellent odor-lingering property, and thus enhancing the preference and the odor strength thereof. In addition, the fragrance composition of the present invention can be used to give an overall positive effect to a product and impart natural sense of vanilla.

DESCRIPTION OF EMBODIMENTS

Hereinafter, a fragrance composition of the present invention and a product blended with said fragrance composition will be described specifically.

The fragrance composition of the present invention comprises:

A) one or more selected from the group consisting of vanillyl alcohol, ethylvanillyl alcohol, isovanillyl alcohol and veratryl alcohol; and B) one or more selected from the group consisting of 2-ethoxy-4-methylphenol, 2-methoxy-4-methylphenol, 2-ethoxy-5-methylphenol, 2-ethoxy-4-ethylphenol, 2-ethoxy-5-ethylphenol, 2-methoxy-p-cresol methyl carbonate and 2-ethoxy-5-(1-propenyl)-phenol (also known as vanitrope), wherein the total content of component A and component B in the fragrance composition is 0.01-90% by mass, and the mixing ratio of component A and component B (on a mass basis) is in a range of 99:1-70:30.

As mentioned above, the fragrance composition of the present invention is obtained by mixing a specific vanillyl alcohol (specifically, one or more selected from the group consisting of vanillyl alcohol, ethylvanillyl alcohol, isovanillyl alcohol and veratryl alcohol, also referred to as "component A") with an alkoxy phenol or a methyl carbonate ester thereof (specifically, one or more selected from the group consisting of 2-ethoxy-4-methylphenol, 2-methoxy-4-methylphenol, 2-ethoxy-5-methylphenol, 2-ethoxy-4-ethylphenol, 2-ethoxy-5-ethylphenol, 2-methoxy-p-cresol methyl carbonate and 2-ethoxy-5-(1-propenyl)-phenol (also known as vanitrope), also referred to as "component B") at a specific ratio. Since the fragrance composition of the present invention can have a vanillin-like odor property with sufficient strength by having the above-described composition, it can favorably be utilized as an alternative material for vanillin or ethyl vanillin. In addition, by mixing component A and component B at a specific ratio, the fragrance composition of the present invention can mask the unpleasant phenol malodor inherent to some of the alkoxy phenols and the methyl carbonate esters thereof, and can impart natural sense of vanilla.

The fragrance composition of the present invention uses components A and B that are chemically stable compounds even under an alkaline condition, an oxygen-existing condition, a temperature condition, a light exposure condition or the like. Therefore, deterioration or discoloration of the odor can be suppressed even in a vehicle of soap, shampoo or an alcoholic composition, and thus a vanilla odor property can be imparted to a variety of products.

In addition, there is no problem in using the fragrance composition of the present invention with vanillins (specifically, one or more selected from the group consisting of vanillin, ethyl vanillin, isovanillin and methyl vanillin). According to the intended purpose or usage, for example, for the purpose of improving odor of other fragrances and cosmetics, a vanillin can be blend in the fragrance composition of the present invention to further enhance the sense of vanilla.

As described above, the fragrance composition of the present invention contains a vanillyl alcohol (component A), an alkoxy phenol or a methyl carbonate ester thereof (component B).

A vanillyl alcohol can be obtained by reducing a corresponding vanillin by a known method, for example, by reacting sodium borohydride, or by hydrogenating in a suitable solvent in the presence of a nickel catalyst. Vanillyl alcohols are known substances, where odor properties of some compounds (vanillyl alcohols) are known but have not actually been used as a flavor and/or fragrance and have been unnoticed heretofore. This time, the present inventors have conducted a stability test for these compounds by comparing with vanillin or ethyl vanillin, as a result of which found that they were stable even under heat or light and also in various product bases, indicating a possibility of them to be an alternative material for vanillin or ethyl vanillin.

Although the odor strength of vanillyl alcohols is slightly weaker than that of vanillin, they have a vanillin-like odor property. In order to compensate for this weakness of odor strength, the present inventors have conducted a number of experiments by adding various compounds, as a result of which found that addition of an alkoxy phenol or a methyl carbonate ester thereof, particularly 2-ethoxy-4-methylphenol, can effectively augment the odor strength, and can result a sweet isoeugenol-like vanillin-like composition that is comparable to the odor strength of vanillin or ethyl vanillin.

According to the present invention, one or more selected from the group consisting of vanillyl alcohol, ethylvanillyl alcohol, isovanillyl alcohol and veratryl alcohol is used as "a vanillyl alcohol". Among them, ethylvanillyl alcohol is particularly preferable because it has an odor quality and an odor strength similar to vanillin.

Furthermore, one or more selected from the group consisting of 2-ethoxy-4-methylphenol, 2-methoxy-4-methylphenol, 2-ethoxy-5-methylphenol, 2-ethoxy-4-ethylphenol, 2-ethoxy-5-ethylphenol, 2-methoxy-p-cresol methyl carbonate and 2-ethoxy-5-(1-propenyl)-phenol (also known as vanitrope) is used as "an alkoxy phenol or a methyl carbonate ester thereof". Among them, 2-ethoxy-4-methylphenol is particularly preferable because it can impart an odor strength that contributes to the top note as well as a sweet isoeugenol-like odor property.

The fragrance composition of the present invention can have a desired odor sustainability by appropriately regulating the total content of components A and B as well as the mixing ratio of components A and B to enhance the effect of the odor-lingering property.

Specifically, in the fragrance composition of the present invention, the total content of components A and B is 0.01-90% by mass, preferably 0.1% by mass or more and more preferably 1% by mass or more, while preferably 50% by mass or less and more preferably 30% by mass or less, in terms of odor quality and odor strength.

Moreover, the mixing ratio (on a mass basis) of components A and B is in a range of 99:1 to 70:30, preferably in a range of 95:5 to 75:25, and more preferably in a range of 92.5:7.5 to 87.5:12.5, in terms of odor quality. If the proportion of component B exceeds 30% by mass, unpleasant phenol malodor inherent to some of component B can be sensed, which is unsuitable as an alternative material for vanillin or ethyl vanillin.

In a preferable aspect of the present invention, the fragrance composition of the present invention is excellent in odor performance and odor strength. Additionally, the fragrance composition of the present invention has an excellent vanilla-like odor property with high preference, whose aromatic strength is high with a remarkable odor sustainability.

While the fragrance composition of the present invention can be used as a fragrance composition having an excellent vanilla-like odor property with high preference by itself, the fragrance composition of the present invention may also be used, for example, for the purpose of improving the odor of other fragrances and cosmetics.

If necessary, the fragrance composition of the present invention may contain a vanillin (also referred to as "component C") according to the intended purpose or usage.

As a "vanillin" used with the present invention, one or more selected from the group consisting of vanillin, ethyl vanillin, isovanillin and methyl vanillin can be used. Among them, vanillin and ethyl vanillin are preferable in terms of odor strength and economic perspective.

In the fragrance composition of the present invention, the content of the vanillin (component C) is preferably 0.001-30% by mass, more preferably 0.01-20% by mass, and still more preferably 0.1-10% by mass.

Furthermore, if necessary, an antioxidant (also referred to as "component D") may further be blended in the fragrance composition of the present invention for the purpose of suppressing discoloration of the fragrance composition or deterioration of the odor more effectively. Any antioxidant can be used without particular limitation as long as it is a compound that is generally known to have an antioxidant effect. Specific examples include butylated hydroxytoluene (BHT), butylated hydroxyanisole (BHA), β-naphthol, phenyl-α-naphthylamine, tetramethyldiamino diphenylmethane, vitamin E (α-tocopherol, β-tocopherol, γ-tocopherol, δ-tocopherol), vitamin C (L-ascorbic acid) and quercetin. Among them, butylated hydroxytoluene (BHT), butylated hydroxyanisole (BHA) and tocopherol may favorably be used. One or more antioxidants may be used in combination.

In the fragrance composition of the present invention, the content of the antioxidant (component D) is preferably 0.0001-10% by mass, more preferably 0.001-5% by mass, and still more preferably 0.01-3% by mass.

Besides components A and B, the fragrance composition of the present invention may further be blended with a flavor and/or fragrance component that is usually used by those skilled in the art, according to the intended purpose or usage. Examples of other flavor and/or fragrance components include various synthetic aroma chemicals, natural essential oils, synthetic essential oils, citrus oils and animal flavor and/or fragrance materials. For example, a wide range of flavor and/or fragrance components described in Arctander S. "Perfume and Flavor Chemicals" published by the author, Montclair, N.J. (U.S.A.), 1969 can be used.

Typical examples among these flavor and/or fragrance components include α-pinene, limonene, cis-3-hexenol, phenylethyl alcohol, styrallyl acetate, eugenol, rose oxide, linalool, benzaldehyde, methyl dihydrojasmonate and Thesaron (manufactured by Takasago International Corporation).

For example, when a natural essential oil such as bergamot oil, galbanum oil, lemon oil, geranium oil, lavender oil or mandarin oil is blended with the mixture of components A and B, a novel fragrance composition that makes the odor and the odor inherent to the natural essential oil to be mild, rich and fresh to give high preference, and that enhances diffusion property and retention property to give sustainability can be prepared.

Additionally, the fragrance composition of the present invention can be blended with one or more commonly used flavor and/or fragrance retaining agents. Specific examples of such flavor and/or fragrance retaining agents include ethylene glycol, propylene glycol, dipropylene glycol, glycerin, hexyl glycol, benzyl benzoate, triethyl citrate, diethyl phthalate, Hercolyn (methyl abietate), and medium chain fatty acid triglyceride.

A product that can be odored using the fragrance composition of the present invention is not particularly limited as long as the product needs to be added with such odor. Preferable examples include: fragrances and cosmetics such as fragrance products, basic cosmetics, makeup cosmetics, hair-care cosmetics and sunscreen cosmetics; quasi-drugs such as pharmaceutical cosmetics; toiletry products such as hair-care products, soap, body cleaning agents and bath agents; and goods such as detergents, fabric softeners, cleaning agents, kitchen detergents, bleaching agents, aerosols, deodorants/air fresheners, sanitary products and stationery.

Examples of fragrance products include perfume, eau de parfum, eau de toilette and eau de cologne.

Examples of basic cosmetics include face washing cream, vanishing cream, cleansing cream, cold cream, massage cream, emulsion, skin lotion, liquid cosmetics, pack and makeup remover.

Examples of makeup cosmetics include foundation, face powder, pressed face powder, talcum powder, lipstick, lip cream, blush, eyeliner, mascara, eye shadow, eyebrow pencil, eye pack, manicure and nail enamel remover.

Examples of hair-care cosmetics include pomade, brilliantine, hair setting lotion, hair stick, hair solid, hair oil, hair treatment, hair cream, hair tonic, hair liquid, hair spray, bandoline, hair growing agents and hair dyeing agent.

Examples of sunscreen cosmetics include suntan products and sunscreen products.

Examples of pharmaceutical cosmetics include antiperspirant, after-shave lotion and gel, permanent wave agent, medicated soap, medicated shampoo and medicated skin cosmetics.

Examples of hair-care products include shampoo, hair rinse, two-in-one shampoo, hair conditioner, hair treatment and hair pack.

Examples of soap include cosmetic soap, bath soap, perfumed soap, transparent soap and synthetic soap.

Examples of body cleaning agents include body soap, body shampoo, hand soap and face cream.

Examples of bath agents include bath additives (bath salt, bath tablet, bath liquid, etc.), foam bath (bubble bath, etc.), bath oil (bath perfume, bath capsule, etc), milk bath, bath jelly and bath cube.

Examples of detergents include heavy-duty laundry detergent, light-duty laundry detergent, liquid detergent, laundry soap, compact detergent and powdery soap.

Examples of fabric softeners include softener and furniture care.

Examples of cleaning agents include cleanser, household cleaner, toilet cleaning agents, bathroom cleaning agents, glass cleaner, mold removing agents and drain-pipe cleaning agents.

Examples of kitchen detergents include kitchen soap, synthetic kitchen soap and dishwashing detergents.

Examples of bleaching agents include oxidized bleaching agents (chlorine-based bleaching agents, oxygen-based bleaching agents, etc.), reduced bleaching agents (sulfur-based bleaching agents, etc.) and optical bleaching agents.

Examples of aerosols include spray types and powder sprays.

Examples of deodorant/air freshener include solid types, gel types and liquid types (water-based, oil-based).

Examples of sanitary products include tissues and toilet paper.

Examples of stationery include eraser, pencil, notebook and seal.

The dosage form of the fragrance composition of the present invention is not particularly limited. For example, it may directly take the form of the mixture of component A, component B and any various components as it is.

As other dosage forms, any dosage form may be selected and used according to the purpose, including, for example:

liquid forms dissolved in alcohols, polyalcohols such as propylene glycol, glycerin and dipropylene glycol, or esters such as triethyl citrate, benzyl benzoate and diethyl phthalate;

emulsion forms emulsified with emulsifiers such as glycerin fatty acid ester and sucrose fatty acid ester;

powder forms coated with excipients such as natural gummy matters (gum arabic, tragacanth gum, etc.), gelatin and dextrin; and solubilized or dispersed forms that are solubilized or dispersed with surfactants (for example, nonionic surfactants, anion surfactants, cationic surfactants, amphoteric surfactants, etc.).

Alternatively, any dosage form, such as a microcapsule form obtained by treating with a capsulating agent, may be used according to the purpose.

Moreover, the fragrance composition of the present invention can be stabilized and made to have sustained releasability by clathrating in a clathrate agent such as cyclodextrin. This is suitable when the form of the end product is, for example, a liquid form, a solid form, a powdered form, a gel form, a mist form or an aerosol form, which may appropriately be selected and used according to the form of the end product.

EXAMPLES

Hereinafter, the present invention will be described specifically by way of examples, although the present invention should not be limited in any way to these examples. In addition, various changes and amendments can be made without departing from the scope of the present invention. Unless otherwise stated, the units used for formulation hereafter are such that: "%" represents "% by mass" and composition ratios represent mass ratios.

Example 1

Blending Ratio of Components A and B, and Odor Quality and Strength Thereof

Ethyl vanillyl alcohol was used as component A while 2-ethoxy-4-methylphenol was used as component 13 to prepare 10% ethanol solutions having the blending ratios (mass ratios) of ethylvanillyl alcohol and 2-ethoxy-4-methylphenol from 100:0 to 75:25 at 5% intervals. Blotters were perfumed with the resultants for evaluation by 10 panelists having five or more years of experience. The evaluation results are shown in Table 1.

TABLE 1

| Mixing ratio of Ethylvanillyl alcohol/ 2-Ethoxy-4-methylphenol | Odor quality and strength | Evaluation |
|---|---|---|
| 100:0 | Weak | D |
| 95:5 | Sweetness comes out | B |
| 90:10 | Sweetest and isoeugenol-like | A |
| 85:15 | Slightly weak | B |
| 80:20 | Slightly phenolic with strong sweetness | B |
| 75:25 | Slightly phenolic with slightly weak sweetness | C |

As can be appreciated from Table 1, sweet isoeugenol-like vanillin-like odor was found to be expressed by mixing ethylvanillyl alcohol and 2-ethoxy-4-methylphenol at a predetermined blending ratio. Among them, the 90:10 mixture was found to express the sweetest, strong isoeugenol-like, vanillin-like odor. Although the strength of ethylvanillyl alcohol alone (100:0) was weak, the odor strength was augmented and the odor quality gained sweetness by blending a small amount of 2-ethoxy-4-methylphenol.

The unpleasant phenol malodor originating from 2-ethoxy-4-methylphenol was insensible up to 15% by mass and slightly sensible from 20% by mass, but was masked by blending ethylvanillyl alcohol.

As can be appreciated from these results, while ethylvanillyl alcohol and 2-ethoxy-4-methylphenol are compounds having different odor quality and strength from each other, their respective merits were successfully elicited both in terms of odor quality and strength by carefully examining the blending ratios.

Example 2

Chromatic Fading Tests Under Heat and Light for Products Containing Component A or B Alone Vanillyl alcohol, ethylvanillyl alcohol and isovanillyl alcohol were each used as component A while 2-ethoxy-4-methylphenol, 2-methoxy-p-cresol methyl carbonate and 2-ethoxy-5-(1-propenyl)-phenol (vanitrope) were each used as component B to prepare 1% dipropylene glycol solutions, which were blended in bases for shampoo, liquid detergent or soap, respectively. The resulting blended products were placed in environments at 5° C., 45° C. or under sunlight exposure (room temperature) to observe changes in the color tones after 4 weeks. The results of evaluations are shown in Table 2 using vanillin and ethyl vanillin under each condition as benchmarks.

TABLE 2

<Change in color tones after 4 weeks>

| | | Shampoo 0.8% | | | Liquid detergent 0.5% | | | Soap 1.0% | | |
|---|---|---|---|---|---|---|---|---|---|---|
| Base Mixed amount | | | Room temperature (Sunlight | | | Room temperature (Sunlight | | | Room temperature (Sunlight | |
| No. | Compound | 5° C. | exposure) | 45° C. | 5° C. | exposure) | 45° C. | 5° C. | exposure) | 45° C. |
| 1 | Vanillin | C | C | C | C | C | C | C | C | C |
| 2 | Ethyl vanillin | C | C | C | C | C | C | C | C | C |
| 3 | Vanillyl alcohol | C | C | A | A | A | B | A | C | B |
| 4 | Ethylvanillyl alcohol | C | B | A | A | A | B | B | B | B |
| 5 | Isovanillyl alcohol | C | B | A | A | A | B | B | B | B |
| 6 | 2-Ethoxy-4-methylphenol | C | B | A | A | A | B | A | A | A |
| 7 | 2-Methoxy-p-cresol methyl carbonate | C | A | A | A | A | B | A | A | A |
| 8 | Vanitrope | C | B | A | A | A | B | A | A | A |

Criteria of evaluation
A: Significantly less chromatically faded compared to C
B: Slightly less chromatically faded compared to C
C: Benchmark (standard)
D: Slightly chromatically faded compared to C
E: Significantly chromatically faded compared to C As a result, both components A and B were found to be significant compared to vanillin and ethyl vanillin. In particular, although ethylvanillyl alcohol was evaluated B in shampoo under sunlight exposure condition, in liquid detergent under 45° C. condition and in strong alkaline soap, it was found to be highly significant compared to vanillin and ethyl vanillin. 2-Ethoxy-4-methylphenol was also evaluated B in shampoo under sunlight exposure condition and in liquid detergent under 45° C. condition, but apart from those, it was evaluated A showing higher significance over vanillin and ethyl vanillin. Since veratryl alcohol was obtained by methoxylating phenol of vanillyl alcohol, it is considered to give more stable result than ethylvanillyl alcohol. Since 2-methoxy-4-methylphenol, 2-ethoxy-5-methylphenol, 2-ethoxy-4-ethylphenol and 2-ethoxy-5-ethylphenol have similar chemical structure to 2-ethoxy-4-methylphenol, they are considered to give results similar to those of 2-ethoxy-4-methylphenol.

Example 3

Chromatic Fading Tests Under Heat and Light for Products Containing Component A or B Alone, and Changes in Odor Quality Thereof 10% ethanol solutions of ethylvanillyl alcohol, 2-ethoxy-4-methylphenol, vanillin and ethyl vanillin were prepared and placed in environments at 5° C., room temperature, 45° C. or under sunlight exposure (room temperature) to observe changes in the color tones and the odor quality after 2 weeks. A sample kept at 5° C. was used as a standard. The results are shown in Table 3.

TABLE 3

| | 5° C. | | Room temperature | | 45° C. | | Light irradiation | |
|---|---|---|---|---|---|---|---|---|
| Compound | Change in color tone | Change in odor quality | Change in color tone | Change in odor quality | Change in color tone | Change in odor quality | Change in color tone | Change in odor quality |
| Ethylvanillyl alcohol 10% EtOH solution | Standard | Standard | No change | No change | Light brown | Slightly weak strength | No change | Slightly weak strength |
| 2-Ethoxy-4-methylphenol 10% EtOH solution | Standard | Standard | No change | No change | No change | No change | No change | No change |
| Vanillin 10% EtOH solution | Standard | Standard | No change | No change | Pale yellow | No change | Brown | No change |
| Ethylvanillin 10% EtOH solution | Standard | Standard | No change | No change | No change | Slightly balsamic, phenolic | Brown | Balsamic, phenolic |

As a result, 2-ethoxy-4-methylphenol showed no change in the color tone and the odor quality at room temperature, 45° C. and under sunlight exposure (room temperature). Ethylvanillyl alcohol did not show change in the color tone and the odor quality at room temperature, but showed slight discoloration under 45° C. condition, and the strength of odor slightly weakened under 45° C. and sunlight exposure (room temperature) conditions. Meanwhile, vanillin changed to pale yellow under 45° C. condition, and both vanillin and ethyl vanillin browned under sunlight exposure (room temperature) condition. Ethyl vanillin also showed change in the odor quality under 45° C. and sunlight exposure (room temperature) conditions.

With respect to component A, vanillyl alcohol and isovanillyl alcohol are expected to give similar results to those of ethylvanillyl alcohol due to their similar structures. Since veratryl alcohol was obtained by methoxylating phenol of vanillyl alcohol, it is considered to give more stable result than ethylvanillyl alcohol. With respect to component B, 2-ethoxy-5-methylphenol, 2-ethoxy-4-ethylphenol and 2-ethoxy-5-ethylphenol are considered to have equivalent stability and are expected to result similar changes in the color tone and the odor quality to 2-ethoxy-4-methylphenol since they have similar chemical structures. In addition, 2-methoxy-p-cresol methyl carbonate and 2-ethoxy-5-(1-propenyl)-phenol are also considered to give results similar to those of 2-ethoxy-4-methylphenol based on the experiment results obtained in Example 2.

Example 4

Chromatic Fading Tests Under Heat and Light as Mixture, and Changes in Odor Quality Thereof (Part 1)

10% ethanol solutions were prepared by changing the mixture ratio of ethylvanillyl alcohol (EVA) and 2-ethoxy-4-methylphenol from 95:5 to 70:30 at 5% intervals, and placed in environments at 5° C., room temperature, 45° C. or under sunlight exposure (room temperature) to observe changes in the color tones and the odor quality after 2 weeks. A sample kept at 5° C. was used as a standard. The results are shown in Table 4.

TABLE 4

| | 5° C. | | Room temperature | | 45° C. | | Light irradiation | |
|---|---|---|---|---|---|---|---|---|
| Compound | Change in color tone | Change in odor quality | Change in color tone | Change in odor quality | Change in color tone | Change in odor quality | Change in color tone | Change in odor quality |
| EVA: 2-Ethoxy-4-melhylphenol = 95:5 10% EtOH solution | Standard | Standard | No change | No change | Pale yellow | No change | No change | No change |
| EVA: 2-Ethoxy-4-methylphenol = 90:10 10% EtOH solution | Standard | Standard | No change | No change | Pale yellow | No change | No change | No change |
| EVA: 2-Ethoxy-4-methylphenol = 85:15 10% EtOH solution | Standard | Standard | No change | No change | Pale yellow | No change | No change | No change |
| EVA: 2-Ethoxy-4-methylphenol = 80:20 10% EtOH solution | Standard | Standard | No change | No change | Pale yellow | No change | No change | No change |
| EVA: 2-Ethoxy-4-methylphenol = 75:25 10% EtOH solution | Standard | Standard | No change | No change | Pale yellow | No change | No change | No change |
| EVA: 2-Ethoxy-4-methylphenol = 70:30 10% EtOH solution | Standard | Standard | No change | No change | Pale yellow | No change | No change | No change |

As a result, none of the samples generally showed change in the odor quality but changes to pale yellow were seen under 45° C. condition.

Furthermore, the same experiment was conducted by changing the solvent to an aprotic solvent BB (Benzyl benzoate). The results are shown in Table 5.

TABLE 5

| | 5° C. | | Room temperature | | 45° C. | | Light irradiation | |
|---|---|---|---|---|---|---|---|---|
| Compound | Change in color tone | Change in odor quality | Change in color tone | Change in odor quality | Change in color tone | Change in odor quality | Change in color tone | Change in odor quality |
| EVA: 2-Ethoxy-4-methylphenol = 95:5 10% BB solution | Standard | Standard | No change | No change | No change | No change | No change | No change |

TABLE 5-continued

| Compound | 5° C. | | Room temperature | | 45° C. | | Light irradiation | |
|---|---|---|---|---|---|---|---|---|
| | Change in color tone | Change in odor quality | Change in color tone | Change in odor quality | Change in color tone | Change in odor quality | Change in color tone | Change in odor quality |
| EVA: 2-Ethoxy-4-methylphenol = 90:10 10% BB solution | Standard | Standard | No change | No change | No change | No change | No change | No change |
| EVA: 2-Ethoxy-4-methylphenol = 85:15 10% BB solution | Standard | Standard | No change | No change | No change | No change | No change | No change |
| EVA: 2-Ethoxy-4-methylphenol = 80:20 10% BB solution | Standard | Standard | No change | No change | No change | No change | No change | No change |
| EVA: 2-Ethoxy-4-methylphenol = 75:25 10% BB solution | Standard | Standard | No change | No change | No change | No change | No change | No change |
| EVA: 2-Ethoxy-4-methylphenol = 70:30 10% BB solution | Standard | Standard | No change | No change | No change | No change | No change | No change |

As a result, none of the samples showed change in the color tone or the odor quality.

Example 5

Chromatic Fading Tests Under Heat and Light for Products Containing as Mixture, and Changes in Odor Quality Thereof 5% Dipropylene glycol (DPG) solutions were prepared for mixtures of vanillin, ethyl vanillin, ethylvanillyl alcohol, 2-ethoxy-4-methylphenol or vanillin and 2-ethoxy-4-methylphenol at 90:10, a mixture of ethyl vanillin (EV) and 2-ethoxy-4-methylphenol at 90:10, and a mixture of ethylvanillyl alcohol (EVA) and 2-ethoxy-4-methylphenol at 90:10. Each of the prepared DPG solutions was blended in five respective bases of an alcohol solution, shampoo, body soap, softener and bath salt. The resulting blended products were placed in environment at 5° C., room temperature (light shielded), 45° C. or under sunlight exposure (room temperature) to observe changes in the color tones and the odor quality after 4 weeks. The results of evaluations are shown in Tables 6, 7, 9, 11 and 13, using vanillin and ethyl vanillin under the respective conditions as benchmarks. The color tones and odor quality were evaluated on the following five scales, respectively.

Change in Color Tone
C1: No change
C2: Very slight change
C3: Slight change
C4: Changed
C5: Significant change Change in Odor Quality
P1: No change
P2: Very slight change
P3: Slight change
P4: Changed
P5: Significant change Alcohol Solution (10% Solution of 95% Ethanol)

TABLE 6

| Compound | 5° C. | | Room temperature | | 45° C. | | Light irradiation | |
|---|---|---|---|---|---|---|---|---|
| | Change in color tone | Change in odor quality | Change in color tone | Change in odor quality | Change in color tone | Change in odor quality | Change in color tone | Change in odor quality |
| Vanillin 5% DPG solution | C1 | P1 | C1 | P1 | C1 | P2 | C5 | P3 |
| Ethylvanillin 5% DPG solution | C1 | P1 | C1 | P1 | C1 | P1 | C5 | P3 |
| Ethylvanillyl alcohol 5% DPG solution | C1 | P1 | C1 | P1 | C1 | P2 | C3 | P2 |
| 2-Ethoxy-4-methylphenol 5% DPG solution | C1 | P1 | C1 | P1 | C1 | P1 | C1 | P1 |
| Vanillin: 2-Ethoxy-4-methylphenol 5% DPG solution | C1 | P1 | C1 | P1 | C1 | P2 | C3 | P3 |

TABLE 6-continued

| | 5° C. | | Room temperature | | 45° C. | | Light irradiation | |
|---|---|---|---|---|---|---|---|---|
| Compound | Change in color tone | Change in odor quality | Change in color tone | Change in odor quality | Change in color tone | Change in odor quality | Change in color tone | Change in odor quality |
| EV: 2-Ethoxy-4-methylphenol 5% DPG solution | C1 | P1 | C1 | P1 | C1 | P2 | C3 | P2 |
| EVA: 2-Ethoxy-4-methylphenol 5% DPG solution | C1 | P1 | C1 | P1 | C1 | P2 | C2 | P3 |

In the alcohol solution, 2-ethoxy-4-methylphenol did not show change in the color tone and the note, while ethylvanillyl alcohol showed slight change under 45° C. and light irradiation conditions.

The 90:10 mixture of ethylvanillyl alcohol and 2-ethoxy-4-methylphenol (5% dipropylene glycol solution of EVA: 2-ethoxy-4-methylphenol) as the fragrance composition of the present invention showed slight changes in the odor quality under 45° C. and light irradiation conditions, and a very slight change in the color tone under light irradiation condition, but these changes were in an allowable range.

Here, the alcohol solution were obtained by diluting each of the DPG solutions prepared above in 95% ethanol to a proportion of 10%.

Shampoo (0.5% Solution)

TABLE 7

| | 5° C. | | Room temperature | | 45° C. | | Light irradiation | |
|---|---|---|---|---|---|---|---|---|
| Compound | Change in color tone | Change in odor quality | Change in color tone | Change in odor quality | Change in color tone | Change in odor quality | Change in color tone | Change in odor quality |
| Vanillin 5% DPG solution | C3 | P1 | C3 | P1 | C5 | P2 | C4 | P4 |
| Ethylvanillin 5% DPG solution | C2 | P1 | C3 | P1 | C4 | P2 | C4 | P3 |
| Ethylvanillyl alcohol 5% DPG solution | C1 | P1 | C1 | P1 | C1 | P1 | C2 | P2 |
| 2-Ethoxy-4-methylphenol 5% DPG solution | C1 | P1 | C1 | P1 | C1 | P1 | C1 | P2 |
| Vanillin: 2-Ethoxy-4-methylphenol 5% DPG solution | C3 | P1 | C3 | P2 | C5 | P3 | C4 | P4 |
| EV: 2-Ethoxy-4-methylphenol 5% DPG solution | C2 | P1 | C3 | P1 | C3 | P3 | C3 | P3 |
| EVA: 2-Ethoxy-4-methylphenol 5% DPG solution | C1 | P1 | C1 | P1 | C1 | P2 | C2 | P3 |

There was obvious difference in the change in the color tone and the odor quality between shampoos with and without vanillin or ethyl vanillin. Up to C3 and P3 were allowable. The 90:10 mixture of ethylvanillyl alcohol and 2-ethoxy-4-methylphenol (5% dipropylene glycol solution of EVA: 2-ethoxy-4-methylphenol) as the fragrance composition of the present invention showed slight change in the odor quality under 45° C. and light irradiation conditions, and very slight change in the color tone under light irradiation condition, but these changes were in an allowable range.

Here, the formulation of the shampoo as the specimen was as follows. In this shampoo, each of the DPG solutions prepared above was blended to a proportion of 0.5% to obtain a sample.

TABLE 8

| Formulation (components) | (Mixed amount g) |
|---|---|
| Sodium polyoxyethylene lauryl ether sulfate | 14.00 |
| Lauramidopropyl betaine | 4.00 |
| Coconut oil fatty acid diethanolamide | 3.00 |
| Cationic cellulose | 0.50 |
| Ethylene glycol distearate | 1.00 |
| Ethyl parahydroxybenzoate | 0.25 |

TABLE 8-continued

| Formulation (components) | (Mixed amount g) |
|---|---|
| Citric acid | Moderate amount |
| Sample | 0.50 |
| Purified water | Remainder |
| Total | 100.00 |

Body Soap (1.0% Solution)

TABLE 9

| Compound | 5° C. | | Room temperature | | 45° C. | | Light irradiation | |
|---|---|---|---|---|---|---|---|---|
| | Change in color tone | Change in odor quality | Change in color tone | Change in odor quality | Change in color tone | Change in odor quality | Change in color tone | Change in odor quality |
| Vanillin 5% DPG solution | C1 | P1 | C1 | P1 | C1 | P2 | C5 | P4 |
| Ethylvanillin 5% DPG solution | C1 | P1 | C1 | P1 | C1 | P2 | C5 | P4 |
| Ethylvanillyl alcohol 5% DPG solution | C1 | P1 | C1 | P1 | C2 | P1 | C3 | P3 |
| 2-Ethoxy-4-methylphenol 5% DPG solution | C1 | P1 | C1 | P1 | C1 | P2 | C3 | P3 |
| Vanillin: 2-Ethoxy-4-methylphenol 5% DPG solution | C1 | P1 | C1 | P2 | C4 | P3 | C5 | P4 |
| EV: 2-Ethoxy-4-methylphenol 5% DPG solution | C1 | P1 | C1 | P1 | C1 | P2 | C5 | P3 |
| EVA: 2-Ethoxy-4-methylphenol 5% DPG solution | C1 | P1 | C1 | P1 | C1 | P2 | C3 | P3 |

Similar to shampoo, there was obvious difference in the changes in the color tone and the odor quality between body soaps with and without vanillin or ethyl vanillin. Up to C3 and P3 were allowable. The 90:10 mixture of ethylvanillyl alcohol and 2-ethoxy-4-methylphenol (5% dipropylene glycol solution of EVA: 2-ethoxy-4-methylphenol) as the fragrance composition of the present invention showed slight change in the odor quality under 45° C. and light irradiation conditions, and very slight change in the color tone under the light irradiation condition, but these changes were in an allowable range.

Here, the formulation of the body soap as the specimen was as follows. In this body soap, each of the DPG solutions prepared above was blended to a proportion of 1.0% to obtain a sample.

TABLE 10

| Formulation (components) | (Mixed amount g) |
|---|---|
| Triethanolamine | 9.00 |
| Lauric acid | 6.00 |
| Myristic acid | 9.00 |
| Disodium polyoxyethylene lauryl sulfosuccinate (1E.O.) (42%) | 10.00 |
| Alkyl (C8-C16) glucoside | 8.00 |
| Glyceryl laurate | 1.00 |
| 2-Hydroxyethyl distearate | 2.50 |
| Coconut oil fatty acid diethanolamide | 3.00 |
| Propylene glycol | 5.00 |
| Dibutylhydroxytoluene | 0.05 |
| Edetate disodium | 0.10 |
| Ethyl para-oxybenzoate | 0.20 |
| Methyl para-oxybenzoate | 0.10 |
| Sample | 1.00 |
| Purified water | Remainder |
| Total | 100.00 |

Softener (0.4% Solution)

TABLE 11

| Compound | 5° C. | | Room temperature | | 45° C. | | Light irradiation | |
|---|---|---|---|---|---|---|---|---|
| | Change in color tone | Change in odor quality | Change in color tone | Change in odor quality | Change in color tone | Change in odor quality | Change in color tone | Change in odor quality |
| Vanillin 5% DPG solution | C1 | P1 | C1 | P1 | C1 | P1 | C1 | P4 |
| Ethylvanillin 5% DPG solution | C1 | P1 | C1 | P1 | C1 | P1 | C1 | P4 |
| Ethylvanillyl alcohol 5% DPG solution | C1 | P1 | C1 | P1 | C1 | P2 | C1 | P3 |
| 2-Ethoxy-4-methylphenol 5% DPG solution | C1 | P1 | C1 | P1 | C1 | P1 | C1 | P3 |
| Vanillin: 2-Ethoxy-4-methylphenol 5% DPG solution | C1 | P1 | C1 | P2 | C1 | P3 | C1 | P4 |
| EV: 2-Ethoxy-4-methylphenol 5% DPG solution | C1 | P1 | C1 | P1 | C1 | P2 | C1 | P4 |

TABLE 11-continued

| | 5° C. | | Room temperature | | 45° C. | | Light irradiation | |
|---|---|---|---|---|---|---|---|---|
| Compound | Change in color tone | Change in odor quality | Change in color tone | Change in odor quality | Change in color tone | Change in odor quality | Change in color tone | Change in odor quality |
| EVA: 2-Ethoxy-4-methylphenol 5% DPG solution | C1 | P1 | C1 | P1 | C1 | P2 | C1 | P3 |

In the case of softener, no change in the color tone was observed under any condition. Under light irradiation condition, however, deterioration in the odor quality was seen for softeners containing vanillin or ethyl vanillin. Up to P3 was allowable. The 90:10 mixture of ethylvanillyl alcohol and 2-ethoxy-4-methylphenol (5% dipropylene glycol solution of EVA: 2-ethoxy-4-methylphenol) as the fragrance composition of the present invention showed slight change in the odor quality under 45° C. and light irradiation conditions, but these changes were in an allowable range.

Here, the formulation of the softener as the specimen was as follows. In this softener, each of the DPG solutions prepared above was blended to a proportion of 0.4% to obtain a sample.

TABLE 12

| Formulation (components) | (Mixed amount g) |
|---|---|
| LION SOFTER EQ | 15.00 |
| Leocol TDA-400-75 | 2.00 |
| 10% Calcium chloride aq | 0.50 |
| Disodium polyoxyethylene lauryl sulfosuccinate | 10.00 |
| Dibutylhydroxytoluene | 0.01 |
| 1% NaOH | 1.00 |
| 95% Ethanol | 3.00 |
| Sample | 0.40 |
| Purified water | Remainder |
| Total | 100.00 |

Bath Salt (Mirabilite-Based) (1.0% Blend)

under light irradiation condition. 2-Ethoxy-4-methylphenol also showed deterioration of the odor quality under light irradiation condition, while the 90:10 mixture of ethylvanillyl alcohol and 2-ethoxy-4-methylphenol (5% dipropylene glycol solution of EVA: 2-ethoxy-4-methylphenol) as the fragrance composition of the present invention showed slight change in the odor quality, which was in an allowable range.

Here, the formulation of the bath salt as the specimen was as follows. In this bath salt, each of the DPG solutions prepared above was blended to a proportion of 1.0% to obtain a sample.

TABLE 14

| Formulation (components) | (Mixed amount g) |
|---|---|
| Neutral anhydrous mirabilite | 98.50 |
| Syloid 244 | 0.50 |
| Sample | 1.00 |
| Total | 100.00 |

Example 6

Possibility of Replacement of Vanillin in Fragrance Formulation

Fragrance compositions were formulated according to the fragrance formulations shown below for comparison by 10 specialized panelists having five or more years of experience

TABLE 13

| | 5° C. | | Room temperature | | 45° C. | | Light irradiation | |
|---|---|---|---|---|---|---|---|---|
| Compound | Change in color tone | Change in odor quality | Change in color tone | Change in odor quality | Change in color tone | Change in odor quality | Change in color tone | Change in odor quality |
| Vanillin 5% DPG solution | C1 | P1 | C1 | P1 | C1 | P2 | C1 | P5 |
| Ethylvanillin 5% DPG solution | C1 | P1 | C1 | P1 | C1 | P2 | C1 | P4 |
| Ethylvanillyl alcohol 5% DPG solution | C1 | P1 | C1 | P1 | C1 | P2 | C1 | P3 |
| 2-Ethoxy-4-methylphenol 5% DPG solution | C1 | P1 | C1 | P1 | C1 | P2 | C1 | P4 |
| Vanillin: 2-Ethoxy-4-methylphenol 5% DPG solution | C1 | P1 | C1 | P1 | C1 | P2 | C1 | P4 |
| EV: 2-Ethoxy-4-methylphenol 5% DPG solution | C1 | P1 | C1 | P1 | C1 | P3 | C1 | P4 |
| EVA: 2-Ethoxy-4-methylphenol 5% DPG solution | C1 | P1 | C1 | P1 | C1 | P2 | C1 | P3 |

The bath salts did not show any change in the color tone under the respective conditions but those containing vanillin or ethyl vanillin showed deterioration of the odor quality to find out whether or not vanillin (Vanillin) and ethyl vanillin (Eth Vanillin) can be replaced with ethylvanillyl alcohol (EVA) or a 90:10 mixture of ethylvanillyl alcohol and 2-ethoxy-4-methylphenol (EVA+UV). As a result, ethylvanillyl alcohol had more sense of sweetness than non-vanillin-blended dipropylene glycol (DPG) but its sweetness was weaker than those of vanillin and ethyl vanillin. On the other hand, the 90:10 mixture of ethylvanillyl alcohol and 2-ethoxy-4-methylphenol was closer to vanillin than ethyl vanillin in terms of odor quality, with strength of odor quality being almost equivalent to vanillin.

The fragrance formulations are shown in below.

TABLE 15

| Name | DPG | Vanillin | Eth Vanillin | EVA | EVA + UV |
|---|---|---|---|---|---|
| ACETYL ISO EUGENOL | 10.00 | 10.00 | 10.00 | 10.00 | 10.00 |
| ALLYL CAPROATE | 20.00 | 20.00 | 20.00 | 20.00 | 20.00 |
| BENZALDEHYDE | 3.00 | 3.00 | 3.00 | 3.00 | 3.00 |
| CITRONELLYL ACET | 20.00 | 20.00 | 20.00 | 20.00 | 20.00 |
| COUMARIN | 80.00 | 80.00 | 80.00 | 80.00 | 80.00 |
| DIMETH BENZ CARB BUTY | 10.00 | 10.00 | 10.00 | 10.00 | 10.00 |
| ETH 2-METH BUTY | 5.00 | 5.00 | 5.00 | 5.00 | 5.00 |
| ETH BUTY | 3.00 | 3.00 | 3.00 | 3.00 | 3.00 |
| ETH CAPROATE | 4.00 | 4.00 | 4.00 | 4.00 | 4.00 |
| ETH LINALOOL | 60.00 | 60.00 | 60.00 | 60.00 | 60.00 |
| GALBASCONE BHT | 1.50 | 1.50 | 1.50 | 1.50 | 1.50 |
| HEDIONE | 100.00 | 100.00 | 100.00 | 100.00 | 100.00 |
| HEXEN-1-OL, CIS-3 | 4.00 | 4.00 | 4.00 | 4.00 | 4.00 |
| IONONE, ALPHA | 20.00 | 20.00 | 20.00 | 20.00 | 20.00 |
| IONONE, BETA | 80.00 | 80.00 | 80.00 | 80.00 | 80.00 |
| L-CITRONELLOL | 60.00 | 60.00 | 60.00 | 60.00 | 60.00 |
| LINALOOL SYN | 60.00 | 60.00 | 60.00 | 60.00 | 60.00 |
| MANZANATE | 6.00 | 6.00 | 6.00 | 6.00 | 6.00 |
| MUSCONE, L | 1.00 | 1.00 | 1.00 | 1.00 | 1.00 |
| ORBITONE T | 100.00 | 100.00 | 100.00 | 100.00 | 100.00 |
| PATCHOULY OIL DEIRONIZED | 5.00 | 5.00 | 5.00 | 5.00 | 5.00 |
| RASPBERRY KETONE | 40.00 | 40.00 | 40.00 | 40.00 | 40.00 |
| ROSE OXIDE, LAEVO-CIS | 3.00 | 3.00 | 3.00 | 3.00 | 3.00 |
| SAUVIGNONE 100 | 1.00 | 1.00 | 1.00 | 1.00 | 1.00 |
| THESARON | 10.00 | 10.00 | 10.00 | 10.00 | 10.00 |
| UNDECALACTONE, GAMMA | 80.00 | 80.00 | 80.00 | 80.00 | 80.00 |
| VERDOX | 100.00 | 100.00 | 100.00 | 100.00 | 100.00 |
| DIPROPYLENE GLYCOL | 113.50 | 108.5 | 108.5 | 108.5 | 108.5 |
| VANILLIN | | 5 | | | |
| ETH VANILLIN | | | 5 | | |
| ETH VANILLYL ALC | | | | 5 | 4.5 |
| 2-ETHOXY-4-METHYLPHENOL | | | | | 0.5 |
| Total | 1000.00 | 1000.00 | 1000.00 | 1000.00 | 1000.00 |

INDUSTRIAL APPLICABILITY

Since the fragrance composition of the present invention has a vanilla-like odor property with significantly excellent performance and is chemically stable, it can be blended in a variety of products. The fragrance composition of the present invention is favorable for adding odor to products such as fragrances and cosmetics, toiletry products, quasi-drugs and commodities. In a preferable aspect of the present invention, the fragrance composition of the present invention can be used to give an overall positive effect to a product and impart natural sense of vanilla.

The invention claimed is:

1. A fragrance composition, comprising:
    A) one or more selected from the group consisting of vanillyl alcohol, ethylvanillyl alcohol, isovanillyl alcohol and veratryl alcohol; and
    B) one or more selected from the group consisting of 2-ethoxy-4-methylphenol, 2-methoxy-4-methylphenol, 2-ethoxy-5-methylphenol, 2-ethoxy-4-ethylphenol, 2-ethoxy-5-ethylphenol, and 2-methoxy-p-cresol methyl carbonate,
    wherein the total content of component A and component B in the fragrance composition is 0.01-90% by mass, and the mixing ratio of component A and component B (on a mass basis) is in a range of 99:1-70:30.

2. The fragrance composition according to claim 1, wherein component A is ethylvanillyl alcohol and component B is 2-ethoxy-4-methylphenol.

3. The fragrance composition according to claim 1, which has vanilla-like odor.

4. The fragrance composition according to claim 1, further comprising C) one or more selected from the group consisting of vanillin, ethyl vanillin, isovanillin and methyl vanillin.

5. A product that is any of fragrances and cosmetics, a toiletry product, a quasi-drug or goods blended with the fragrance composition according to claim 1.

6. The fragrance composition according to claim 1, wherein component A is ethylvanillyl alcohol.

7. The fragrance composition according to claim 6, which has a vanilla-like odor.

8. The fragrance composition according to claim 6, further comprising C) one or more selected from the group consisting of vanillin, ethyl vanillin, isovanillin and methyl vanillin.

9. A product that is any of fragrances and cosmetics, a toiletry product, a quasi-drug or goods blended with the fragrance composition according to claim 6.

\* \* \* \* \*